US010683255B2

(12) United States Patent
Eastham et al.

(10) Patent No.: US 10,683,255 B2
(45) Date of Patent: Jun. 16, 2020

(54) PROCESS FOR THE PRODUCTION OF ETHYLENICALLY UNSATURATED CARBOXYLIC ACID ESTERS AND A CATALYST THEREFOR

(71) Applicant: Lucite International UK Limited, Billingham (GB)

(72) Inventors: Graham Ronald Eastham, Redcar (GB); Jonathan Ainsley Iggo, Liverpool (GB); Michael Beaumont, Liverpool (GB)

(73) Assignee: Lucite International UK Limited, Billingham (GB)

( * ) Notice: Subject to any disclaimer, the term of this patent is extended or adjusted under 35 U.S.C. 154(b) by 0 days.

(21) Appl. No.: 16/341,632

(22) PCT Filed: Oct. 11, 2017

(86) PCT No.: PCT/GB2017/053075
§ 371 (c)(1),
(2) Date: Apr. 12, 2019

(87) PCT Pub. No.: WO2018/069702
PCT Pub. Date: Apr. 19, 2018

(65) Prior Publication Data
US 2019/0382332 A1    Dec. 19, 2019

(30) Foreign Application Priority Data
Oct. 14, 2016    (GB) .................................. 1617534.1

(51) Int. Cl.
  *C07C 67/343*    (2006.01)
  *C07C 69/54*    (2006.01)
(52) U.S. Cl.
  CPC ............ *C07C 67/343* (2013.01); *C07C 69/54* (2013.01)

(58) Field of Classification Search
  CPC ............................ C07C 67/343; C07C 69/54
  (Continued)

(56) References Cited

U.S. PATENT DOCUMENTS

| 4,990,662 A | 2/1991 | Hagen et al. |
| 6,544,924 B1 | 4/2003 | Jackson et al. |

FOREIGN PATENT DOCUMENTS

| JP | H0648977 A | 2/1994 |
| WO | 99/64387 A1 | 12/1999 |
| WO | 2016166525 A1 | 10/2016 |

OTHER PUBLICATIONS

Michael Beaumont: "Towards a low temperature, liquid phase methyl methacrylate process through mechanism-guided process design—The the University of Liverpool Repository", Sep. 1, 2016, Abstract (Year: 2016).*

(Continued)

*Primary Examiner* — Deborah D Carr
(74) *Attorney, Agent, or Firm* — Shumaker, Loop & Kendrick, LLP

(57) ABSTRACT

A process for the production of an ethylenically unsaturated carboxylic acid ester, preferably an α,β ethylenically unsaturated carboxylic acid ester is described. The process takes place by the reaction of formaldehyde or a suitable source thereof with a carboxylic acid ester in the presence of a basic metal methyl carbonate co-reactant, wherein the process produces a second basic metal salt and wherein the process includes the step of contacting the second basic metal salt with:
  a) carbon dioxide ($CO_2$) and optionally, methanol, and/or
  b) dimethyl carbonate,
to regenerate the basic metal methyl carbonate co-reactant. The invention includes use of carbon dioxide and/or dimethyl carbonate to regenerate a basic metal methyl carbonate.

29 Claims, 4 Drawing Sheets

(58) Field of Classification Search
USPC .......................................................... 560/210
See application file for complete search history.

(56) References Cited

OTHER PUBLICATIONS

International Preliminary Report on Patentability (IPRP) for PCT/GB2017/053075 dated Apr. 16, 2019 (7 pages).
Beaumont, Michael (2015) Towards a low temperature, liquid phase methyl methacrylate process through mechanism-guided process design. Doctor of Philosophy thesis, University of Liverpool (Abstract Only).
Written Opinion of the International Searching Authority of PCT Application No. PCT/GB2017/053075 dated Dec. 4, 2017 (6 pages).
International Serach Report of PCT International Application No. PCT/GB2017/053075 dated Dec. 4, 2017 (5 pages).
Josef Barthel et al. "Non-Aqueous Electrolyte Solutions in Chemistry and Modern Technology", Topics in Current Chemistry, vol. 111, p. 33-144, (1983).
GB Search Report for GB Patent Appln. No. GB1617534.1, dated Dec. 13, 2016 (4 pages).

\* cited by examiner

PROCESS FOR THE PRODUCTION OF ETHYLENICALLY UNSATURATED CARBOXYLIC ACID ESTERS AND A CATALYST THEREFOR

TECHNICAL FIELD AND BACKGROUND

The present invention relates to a process for the production of ethylenically unsaturated carboxylic acid esters, particularly α, β unsaturated carboxylic acid esters, more particularly acrylic acid esters such as alkyl (alk)acrylates particularly alkyl (meth)acrylates such as methyl (meth)acrylates by the condensation of carboxylic acid esters with formaldehyde or a source thereof in the presence of bases, in particular, but not exclusively, a process for the production of alkyl esters of (meth)acrylic acid, for example, methyl methacrylate, by the condensation of propionic alkyl esters, for example methyl propionate, with formaldehyde or a source thereof in the presence of such a base. The invention is particularly relevant to the production of methyl methacrylate (MMA).

Such esters may be made by reacting an alkanoic ester of the formula $R^3$—$CH_2$—$COOR^4$, where $R^3$ and $R^4$ are each, independently, a suitable substituent known in the art of acrylic compounds such as an alkyl group, especially a lower alkyl group containing, for example, 1-4 carbon atoms, with a suitable methylene source such as formaldehyde. Thus, for instance, alkyl esters of methacrylic acid, especially methyl methacrylate, may be made by the catalytic reaction of methyl propionate, with formaldehyde as a methylene source.

As mentioned above, a known production method for MMA is the catalytic conversion of methyl propionate (MEP) to MMA using formaldehyde. U.S. Pat. No. 6,544,924 describes the production of ethylenically unsaturated acid esters by the catalytic reaction of an alkanoic acid ester, especially methyl propionate, with formaldehyde in the presence of a silica supported catalyst. The production of methyl methacrylate (MMA) from methyl propionate, methanol and formalin using these catalysts was carried out at 350° C. and resulted in yields of MMA and MA between 3 and 12% and selectivities for MMA and MA between 88 and 97%.

It is known that the catalytic efficiency of a catalyst used for the production of an ethylenically unsaturated carboxylic acid ester may decrease over a period of time.

WO00/58298 describes a process for the production of α-methylenelactones and α-substituted hydrocarbylidenes by heating lactones and formaldehyde in the presence of a base. The base may be regenerated by contact with oxygen ($O_2$) at elevated temperatures of up to 500° C. The use of high temperatures is disadvantageous economically.

SUMMARY

According to a first aspect of the present invention there is provided a process for the production of an ethylenically unsaturated carboxylic acid ester, preferably an α,β ethylenically unsaturated carboxylic acid ester, by the reaction of formaldehyde or a suitable source thereof with a carboxylic acid ester in the presence of a basic metal methyl carbonate co-reactant, wherein the process produces a second basic metal salt and wherein the process includes the step of contacting the second basic metal salt with:
  a) carbon dioxide ($CO_2$) and optionally, methanol, and/or
  b) dimethyl carbonate,
to regenerate the basic metal methyl carbonate co-reactant.

Advantageously, the above reaction of formaldehyde or a suitable source thereof with a carboxylic acid ester in the presence of a basic metal methyl carbonate co-reactant produces carbon dioxide ($CO_2$) as a by-product. Suitably, therefore, at least some of the carbon dioxide ($CO_2$) used in the first aspect is by-product carbon dioxide ($CO_2$).

Preferably, when carbon dioxide ($CO_2$) is used, the step of contacting the second basic metal salt with carbon dioxide ($CO_2$) may be carried out in the presence of methanol. When $CO_2$ is used together with dimethyl carbonate, the use of methanol is optional because the dimethyl carbonate acts as a source of methanol after reaction. Therefore, the process of the invention includes the step of contacting the second basic metal salt with:
  a) carbon dioxide ($CO_2$) and
  b) dimethyl carbonate, optionally in the presence of methanol,
to regenerate the basic metal methyl carbonate co-reactant.

Advantageously, the above reaction of formaldehyde or a suitable source thereof with a carboxylic acid ester in the presence of a basic metal methyl carbonate co-reactant produces methanol as a by-product. Suitably, therefore, at least some of the methanol, when used, is such by-product methanol.

The process for the production of the ethylenically unsaturated carboxylic acid ester, preferably α,β ethylenically unsaturated carboxylic acid ester, of the present invention may be a batch or continuous process. Preferably, the process is a continuous process.

DETAILED DESCRIPTION

The reaction may take place in the solid/liquid phase, the liquid phase, the liquid/gas phase or a combination thereof. Preferably, the reaction takes place in the liquid phase. Accordingly, any one or more of the ethylenically unsaturated carboxylic acid ester, the formaldehyde or a suitable source thereof, the carboxylic acid ester, the basic metal methyl carbonate co-reactant and the second basic metal salt may be dissolved in the liquid phase, typically, at least the formaldehyde or a suitable source thereof, the carboxylic acid ester and the basic metal methyl carbonate co-reactant are dissolved in the liquid phase, more typically, at least 80% w/w of each or any aforementioned component is dissolved therein, most typically, at least 90% w/w, especially, at least 95% w/w, most especially, each or any of the aforementioned components are fully dissolved in the liquid phase.

Basic Metal Methyl Carbonate Co-Reactant

Preferably, the basic metal methyl carbonate co-reactant used in the production of an ethylenically unsaturated carboxylic acid ester herein may be any such co-reactant basic enough to deprotonate the carboxylic acid ester, such as methyl propionate. More preferably, the co-reactant is so capable in the liquid phase at the reaction temperature. Typically, the basic metal methyl carbonate co-reactant is a group I or a group II metal methyl carbonate. For the avoidance of doubt, by group I metals as used herein is meant lithium (Li), sodium (Na), potassium (K), rubidium (Rb), and caesium (Cs). For the avoidance of doubt, by group II metals as used herein is meant beryllium (Be), magnesium (Mg), calcium (Ca), strontium (Sr), barium (Ba). Preferably, the group I or group II metal is selected from potassium (K), caesium (Cs), rubidium (Rb) or barium (Ba), more preferably, from caesium (Cs) or rubidium (Rb). Most preferably, the group I or group II metal is selected from caesium (Cs).

Preferably, the basic metal methyl carbonate co-reactant may be selected from potassium methyl carbonate, sodium methyl carbonate, caesium methyl carbonate, rubidium methyl carbonate or barium methyl carbonate, more preferably, caesium methyl carbonate or rubidium methyl carbonate, most preferably, caesium methyl carbonate.

Suitable basic metal methyl carbonate co-reactants include methyl carbonates of caesium (Cs) or rubidium (Rb). Advantageously, the basic metal methyl carbonate co-reactants of the present invention give remarkably high conversions and selectivities for the reaction products of the invention.

Suitable basic group I or II metal methyl carbonate co-reactants are those group I or II metal methyl carbonates which are at least partially soluble in a liquid phase at temperatures up to 300° C., more typically, at temperatures up to 250° C., most preferably, at temperatures up to 200° C.

The basic metal methyl carbonate co-reactant may be present in a liquid phase during the production of an ethylenically unsaturated carboxylic acid ester in any suitable form. Preferably, the basic metal methyl carbonate co-reactant may be dissolved, typically, substantially fully dissolved in the liquid phase or the liquid phase and the basic metal methyl carbonate co-reactant together may be in the form of a slurry, wherein a proportion of the basic metal methyl carbonate co-reactant is dissolved in the liquid phase and a proportion is undissolved and therefore remains in the solid form. More preferably, the basic metal methyl carbonate co-reactant is substantially fully dissolved in the liquid phase.

A continuous reaction for the production of an ethylenically unsaturated carboxylic acid ester may be run with some of the reactants in a solid or gas phase, but is preferably run with the reactants dissolved in the liquid phase.

A batch reaction for the production of an ethylenically unsaturated carboxylic acid ester may be run with some of the reactants in a solid or gas phase, but is preferably run with the reactants dissolved in a liquid phase. Without being bound by theory, in a batch reaction a liquid phase and the basic metal methyl carbonate co-reactant together may be in the form of a slurry at the beginning of the production of an ethylenically unsaturated carboxylic acid ester but more of the basic metal methyl carbonate co-reactant may become dissolved in the liquid phase as the reaction progresses due to the formation of methanol, in which the basic metal methyl carbonate co-reactant may be more soluble, such that the basic metal methyl carbonate co-reactant may have a higher concentration in the liquid phase at the end of the reaction. For the avoidance of doubt, reference to the amount of basic metal methyl carbonate co-reactant dissolved in the liquid phase is the amount dissolved in the liquid phase when it is at the temperature at which the production of an ethylenically unsaturated carboxylic acid ester will be performed.

In one embodiment, the basic metal methyl carbonate co-reactant used in the production of an ethylenically unsaturated carboxylic acid ester is fully saturated in the liquid phase. Preferably, when the basic metal methyl carbonate co-reactant is fully saturated in the liquid phase, any basic metal methyl carbonate co-reactant that is present in the undissolved form may be able to dissolve in the liquid phase as the dissolved basic metal methyl carbonate co-reactant is reacted.

Preferably, at least part of the basic metal methyl carbonate co-reactant is dissolved in the liquid phase during the production of an ethylenically unsaturated carboxylic acid ester.

Second Basic Metal Salt

The process of the present invention produces a second basic metal salt. The second basic metal salt is typically the corresponding metal salt of the carboxylic acid ester reactant and/or the corresponding metal salt of the ethylenically unsaturated carboxylic acid ester product, preferably α,β ethylenically unsaturated carboxylic acid ester product. For the avoidance of doubt the second basic metal salt may comprise any metal present in the reaction, for example, any metal as introduced in the form of the basic metal methyl carbonate co-reactant. The second basic metal salt may comprise one or more metal. The second basic metal salt may comprise one or both of the metal salt of the carboxylic acid ester reactant and the metal salt of the ethylenically unsaturated carboxylic ester product, more preferably the second basic metal salt herein comprises both the metal salt of the carboxylic acid ester reactant and the metal salt of the ethylenically unsaturated carboxylic ester product.

Accordingly, when the second basic metal salt is the corresponding metal salt of the carboxylic acid ester reactant, the second basic metal salt is typically a metal carboxylate of the following formula:

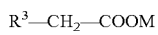

$R^3—CH_2—COOM$ wherein M is a metal of the metal methyl carbonate co-reactant and $R^3$ is hydrogen or a $C_1$ to $C_4$-alkyl group, preferably a methyl group.

Accordingly, when the second basic metal salt is the corresponding metal salt of the ethylenically unsaturated carboxylic acid ester product, preferably α,β ethylenically unsaturated carboxylic acid ester product, the second basic metal salt is typically a metal carboxylate of the following formula:

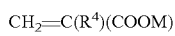

$CH_2=C(R^4)(COOM)$ wherein M is a metal of the basic metal methyl carbonate co-reactant and $R^4$ is hydrogen or a $C_1$ to $C_4$-alkyl group, preferably a methyl group.

Preferably, the second basic metal salt is a group I or group II basic metal salt. More preferably, the second basic metal salt is a group I or group II metal propionate and/or methacrylate. For the avoidance of doubt, group I and group II metals are defined as in relation to the basic metal methyl carbonate co-reactant.

Preferably, the second basic metal salt is selected from potassium propionate, caesium propionate, rubidium propionate, barium propionate, potassium methacrylate, caesium methacrylate, rubidium methacrylate or barium methacrylate, more preferably, from caesium propionate, rubidium propionate, caesium methacrylate or rubidium methacrylate. Most preferably, the second basic metal salt is selected from caesium propionate and/or caesium methacrylate.

Typically, the metal of the second basic metal salt will be the same as the metal of the basic metal methyl carbonate co-reactant.

The second basic metal salt may be present in the liquid phase during the production of an ethylenically unsaturated carboxylic acid ester in any suitable form. Preferably, the second basic metal salt may be dissolved, typically, substantially fully dissolved in the liquid phase or the liquid phase and the second basic metal salt together may be in the form of a slurry, wherein a proportion of the second basic metal salt is dissolved in the liquid phase and a proportion is undissolved and therefore remains in the solid form. More preferably, the second basic metal salt is substantially fully dissolved in the liquid phase.

Preferably, at least part of the second basic metal salt is in the liquid phase.

The second basic metal salt may also act as a co-reactant in the reaction. However, basic metal carboxylates, such as group I or group II metal carboxylates, are relatively poor bases for the process of the invention and are not able to bring about sufficient deprotonation of the carboxylic acid ester reactant to permit an acceptable rate of reaction, particularly on an industrial scale. Accordingly, the process of the present invention includes the step of contacting the second basic metal salt with carbon dioxide (CO2) and optionally, methanol, and/or dimethyl carbonate, to regenerate the basic metal methyl carbonate co-reactant. As the basic metal methyl carbonate co-reactant is more basic than the second basic metal salt it is able to bring about sufficient deprotonation of the carboxylic acid ester reactant to permit an acceptable rate of reaction. Accordingly, it has surprisingly been found that the process of the present invention enables the production of an ethylenically unsaturated carboxylic acid ester, preferably an α,ß ethylenically unsaturated carboxylic acid ester, by the reaction of formaldehyde or a suitable source thereof with a carboxylic acid ester to become more commercially viable.

The step of contacting the second basic metal salt with carbon dioxide ($CO_2$) and optionally, methanol, and/or dimethyl carbonate, results in the regeneration of the basic metal methyl carbonate co-reactant. Accordingly, therefore, the regenerated basic metal methyl carbonated co-reactant is the same as the basic metal methyl carbonate co-reactant.

Preferably, the regenerated basic metal methyl carbonate co-reactant is a group I or group II metal methyl carbonate. Preferably, the regenerated basic metal methyl carbonate co-reactant may be selected from potassium methyl carbonate, sodium methyl carbonate, caesium methyl carbonate, rubidium methyl carbonate or barium methyl carbonate, more preferably, caesium methyl carbonate or rubidium methyl carbonate, most preferably, caesium methyl carbonate.

Preferably, the regenerated basic metal methyl carbonate co-reactant is caesium methyl carbonate.

The regenerated basic metal methyl carbonate co-reactant may be present in the liquid phase during the production of an ethylenically unsaturated carboxylic acid ester in any suitable form. Preferably, the regenerated basic metal methyl carbonate co-reactant may be dissolved, typically, substantially fully dissolved in the liquid phase or the liquid phase and the regenerated basic metal methyl carbonate co-reactant together may be in the form of a slurry, wherein a proportion of the regenerated basic metal methyl carbonate co-reactant is dissolved in the liquid phase and a proportion is undissolved and therefore remains in the solid form. More preferably, the regenerated basic metal methyl carbonate co-reactant is substantially fully dissolved in a liquid phase.

Preferably, at least part of the regenerated basic metal methyl carbonate co-reactant is in the liquid phase.

Advantageously, the regenerated basic metal methyl carbonate co-reactant produced via the step of contacting the second basic metal salt with carbon dioxide ($CO_2$) and optionally, methanol, and/or dimethyl carbonate as defined herein, is more basic than the second basic metal salts and are thus better able to bring about deprotonation of the carboxylic acid ester reactant. Accordingly, it has surprisingly been found by the present inventors that the regenerated basic metal methyl carbonate co-reactant produced via the step of contacting the second basic metal salt with carbon dioxide ($CO_2$) and optionally, methanol, and/or dimethyl carbonate, is basic enough to bring about sufficient deprotonation of the carboxylic acid ester reactant. Preferably, herein at least 30% of the base metal during a continuous process is in the form of the basic metal methyl carbonate for the further conversion of the acid ester to the product.

Preferably, the step of contacting the second basic metal salt with carbon dioxide ($CO_2$) and optionally, methanol, and/or dimethyl carbonate, is carried out at a temperature below about 250° C. Preferably, the step of contacting the second basic metal salt with carbon dioxide ($CO_2$) and optionally, methanol, and/or dimethyl carbonate, is carried at a temperature between about 100° C. and 250° C., more preferably, between about 130° C. and 220° C., most preferably, between about 150° C. and 200° C.

Preferably, the step of contacting the second basic metal salt with carbon dioxide ($CO_2$) and optionally, methanol, and/or a dimethyl carbonate, is carried out under pressure. Preferably, the step of contacting the second basic metal salt with carbon dioxide ($CO_2$) and/or dimethyl carbonate, is carried out at a pressure of between about atmospheric pressure and 2000 psi, more preferably, between about 100 psi and 1000 psi, most preferably, between about 200 psi and 750 psi.

The methanol, when present, may be additionally added to the reactor or may be present in the liquid phase due to its formation during the production of an ethylenically unsaturated carboxylic acid ester or may be present in the liquid phase due to the use of formaldehyde hemiacetal (alcoform) as the source of formaldehyde.

Advantageously, the step of contacting the second basic metal salt with carbon dioxide ($CO_2$) and optionally, methanol, and/or dimethyl carbonate, may result in the production of the carboxylic acid ester reactant. For example, when carbon dioxide ($CO_2$) in the presence of methanol is used the corresponding methyl ester reactant may be produced. For example, when dimethyl carbonate is used, the corresponding methyl ester reactant may be produced. For example, when carbon dioxide ($CO_2$) and dimethyl carbonate are used, the corresponding methyl ester reactant may be produced.

Advantageously, the carboxylic acid ester produced via the step of contacting the second basic metal salt with carbon dioxide ($CO_2$) and optionally, methanol, and/or dimethyl carbonate, can be recycled back into the reaction.

The amount of methanol, when present, is typically in the range of 0.5 to 500 moles of methanol per mole of basic metal methyl carbonate co-reactant, preferably, 1 to 50 moles of methanol per mole of basic metal methyl carbonate co-reactant, more preferably, 2 to 10 moles of methanol per mole of basic metal methyl carbonate co-reactant, 5 to 10 moles of methanol per mole of basic metal methyl carbonate co-reactant.

Preferably, the step of contacting the second basic metal salt with carbon dioxide ($CO_2$) and optionally, methanol, and/or dimethyl carbonate may be performed over a time period of about 5 minutes to 24 hours, more preferably, over about 30 minutes to 12 hours, most preferably, over about 1 hour to 3 hours.

The step of contacting the second basic metal salt with carbon dioxide ($CO_2$) and optionally, methanol, and/or dimethyl carbonate, may be performed once or multiple times during the process. For example, in a batch reaction for the production of an ethylenically unsaturated carboxylic acid ester the second basic metal salt may be contacted with carbon dioxide ($CO_2$) and optionally, methanol, and/or dimethyl carbonate, once at the end of the reaction. Following the step of contacting the second basic metal salt with carbon dioxide (CO$_2$) and optionally, methanol, and/or dimethyl carbonate, at the end of a batch reaction the resultant regenerated basic metal methyl carbonate co-reactant may be extracted and/or purified from the liquid phase and, for example, used in a further process. In a continuous reaction for the production of an ethylenically unsaturated carboxylic acid ester the second basic metal salt may be contacted with carbon dioxide (CO$_2$) and optionally, methanol, and/or dimethyl carbonate, any suitable number of times and at time intervals suitable to allow the reaction to proceed at an acceptable rate. Alternatively, or additionally, in a continuous reaction for the production of an ethylenically unsaturated carboxylic acid ester the second basic metal salt may be contacted with carbon dioxide (CO$_2$) and optionally, methanol, and/or dimethyl carbonate, continuously.

The basic metal methyl carbonate co-reactant is the same as the regenerated basic metal methyl carbonate co-reactant. Accordingly, the co-reactants of the present invention may act catalytically in that the basic metal methyl carbonate co-reactant may be regenerated from the second basic metal salt by contact with carbon dioxide (CO$_2$) and optionally, methanol, and/or dimethyl carbonate. Accordingly, it has been surprisingly found by the present inventors that the process can be run catalytically. Being able to run the process catalytically is of particular advantage in a continuous process where regeneration of the basic metal methyl carbonate co-reactant allows the process to proceed continuously.

The said basic metal methyl carbonate co-reactant, second basic metal salt and/or regenerated basic metal methyl carbonate may provide from 90 to 100 wt % of the total metal present in the liquid phase, such as from 95, 99, 99.5 or 99.9 wt % of the total metal present in the liquid phase, more preferably substantially 100 wt % of the total metal present in the liquid phase based on the total solid weight of metals present in the liquid phase. Typically, no other metal types are present in the liquid phase for the production of an ethylenically unsaturated carboxylic acid ester above a trace level other than the basic metal salts as defined herein, in particular no metal types other than group I or group II metal salts are present in the liquid phase, more particularly, no metal types other than the group I or group II metal salts as defined more particularly herein.

Formaldehyde

A suitable source of formaldehyde may be a compound of formula I

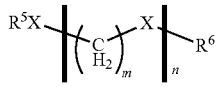

wherein $R^5$ and $R^6$ are independently selected from $C_1$-$C_{12}$ hydrocarbons or H, X is O, n is an integer from 1 to 100, and m is 1.

Preferably, $R^5$ and $R^6$ are independently selected from $C_1$-$C_{12}$ alkyl, alkenyl or aryl as defined herein, or H, more preferably, $C_1$-$C_{10}$ alkyl, or H, most preferably, $C_1$-$C_6$ alkyl or H, especially, methyl or H. Preferably, n is an integer from 1 to 10, more preferably 1 to 5, especially, 1-3. However, other sources of formaldehyde may be used including trioxane.

Therefore, a suitable source of formaldehyde includes any equilibrium composition which may provide a source of formaldehyde. Examples of such include but are not restricted to methylal (1,1 dimethoxymethane), trioxane, polyoxymethylenes $R^1$—O—(CH$_2$—O)$_i$—$R^2$ wherein $R^1$ and/or $R^2$ are alkyl groups or hydrogen, i=1 to 100, paraformaldehyde, formalin (formaldehyde, methanol, water) and other equilibrium compositions such as a mixture of formaldehyde, methanol and methyl propionate. However, sources of formaldehyde containing more than 30% water are not used in the reaction or are at least preferably not used in the reaction.

Typically, the polyoxymethylenes are higher formals or hemiformals of formaldehyde and methanol CH$_3$—O—(CH$_2$—O)$_i$—CH$_3$ ("formal-i") or CH$_3$—O—(CH$_2$—O)$_i$—H ("hemiformal-i"), wherein i=1 to 100, preferably, 1-5, especially 1-3, or other polyoxymethylenes with at least one non methyl terminal group. Therefore, the source of formaldehyde may also be a polyoxymethylene of formula $R^{31}$—O—(CH$_2$—O—)$_i R^{32}$, where $R^{31}$ and $R^{32}$ may be the same or different groups and at least one is selected from a $C_2$-$C_{10}$ alkyl group, for instance $R^{31}$=isobutyl and $R^{32}$=methyl.

Formalin may be used as a feedstock for formaldehyde but is generally de-watered prior to use in the reaction. Preferably, by the term formalin is meant a mixture of formaldehyde:methanol:water in the ratio 25 to 65%:0.01 to 25%:25 to 70% by weight. More preferably, by the term formalin is meant a mixture of formaldehyde:methanol:water in the ratio 30 to 60%:0.03 to 20%:35 to 60% by weight. Most preferably, by the term formalin is meant a mixture of formaldehyde:methanol:water in the ratio 35 to 55%:0.05 to 18%:42 to 53% by weight.

Preferably, a suitable source of formaldehyde may be selected from formalin (formaldehyde, methanol, water), low molecular weight polyformaldehyde (paraformaldehyde), gaseous formaldehyde, formaldehyde hemiacetal (alcoform), trioxane, anhydrous formaldehyde or formaldehyde from a distillative drying process, or other sources of formaldehyde where the level of water is <30%, more preferably, <20% by weight of the level of formaldehyde, more preferably, low molecular weight polyformaldehyde (paraformaldehyde), formaldehyde hemiacetal (alcoform) or anhydrous formaldehyde, most preferably, formaldehyde hemiacetal (alcoform) or anhydrous formaldehyde, especially, a suitable source of formaldehyde may be formaldehyde hemiacetal (alcoform). The use of paraformaldehyde, trioxane, anhydrous formaldehyde and formaldehyde hemiacetal (alcoform), especially, formaldehyde hemiacetal (alcofrom) is preferred since this reduces the need to remove water from the process. The suitable source of formaldehyde may be generated by a distillative drying process such as that described in WO9964387, in which case it may contain, in addition to formaldehyde, methanol and low levels of water, a solvent, most suitably methyl propionate used to assist in the distillative dehydration.

The formaldehyde-containing product described in WO9964387 and suitable as a source of formaldehyde for the present invention is obtained from a formaldehyde solution comprising formaldehyde, water and methanol, wherein said formaldehyde-containing product contains substantially less water than said formaldehyde solution. The formaldehyde-containing product is obtained by a process comprising distilling a formaldehyde solution in the presence of a water entraining compound, such as methyl propionate, such that the formaldehyde containing product is recovered as a complex with methanol and also typically includes the water entraining compound. The process of distilling the formaldehyde may be integrated with the process of the present invention so that the formaldehyde-containing product is supplied directly to present process. Advantageously, methyl propionate may also be present in this source of formaldehyde so that the methyl propionate and formaldehyde and methanol may all be supplied from such a reactive distillation product stream.

Preferably, the reaction mixture, for example the mixture comprising formaldehyde or a suitable source thereof and a carboxylic acid ester, contains less than about 5% water by weight (w/w). More preferably, the reaction mixture, for example the mixture comprising formaldehyde or a suitable source thereof and a carboxylic acid ester, contains less than about 2% water by weight. Most preferably, the reaction mixture, for example the mixture comprising formaldehyde or a suitable source thereof and a carboxylic acid ester, may contain from about 0.1 to 1.0% water by weight.

Preferably, the formaldehyde or suitable source thereof may have a water content of less than about 15% by weight (w/w), more preferably less than about 5% w/w, most preferably less than about 1% w/w. Preferably, the formaldehyde or suitable source thereof is essentially anhydrous.

In certain embodiments, the formaldehyde or suitable source thereof is formaldehyde hemiacetal (alcoform). Advantageously, the use of formaldehyde hemiacetal (alcoform) provides anhydrous formaldehyde.

Solvent

As detailed above, the formaldehyde or suitable source thereof and carboxylic acid ester and the first basic metal salt co-reactant, second basic metal salt and/or increased basicity metal salt co-reactant are preferably dissolved in the liquid phase. This liquid phase may include a solvent for the reaction.

Accordingly, the process of the present invention may optionally further comprise one or more solvents.

Preferably, the solvent is wholly or substantially aprotic. Suitable aprotic solvents are tabulated in Table A-1, pp 112-114, of "Non-Aqueous Elelctrolyte Solutions in Chemistry and Modern Technology" by Josef Barthel, Heiner-J. Gores, Georg Schmeer and Rudolf Wachter, Topics in Current Chemistry, Vol. 111, page 33, 1983, under the headings "Aprotic protophilic solvents", "Aprotic protophobic solvents", "Low permittivity electron donor solvents" and "Inert solvents". Preferably, the solvent is an aprotic protophilic solvent or an aprotic photophobic solvent, more preferably, an aprotic protophilic solvent. Preferably the solvent is selected from dimethyl formamide, diethyl formamide, dimethylacetamide (DMAc), 1,3-dimethyl-3,4,5,6-tetrahydro-2(1H)-pyrimidinone (DMPU), 1,3-dimethyl-2-imidazolidinone (DMEU or DMI), 3-methyl-2-oxazolidinone, propylene carbonate, diethylacetamide, 1-methyl-2-pyrrolidinone, hexamethylphosphoric triamide, pyridine, tetramethyl urea, dimethylsulfoxide, acetonitrile, propionitrile, benzonitrile, acetone, 2-butanone, 3-pentanone, acetophenone, nitromethane, nitrobenzene, tetrahydrothiophene 1,1-dioxide (sulfolane), diethyl ether, diisopropyl ether, 1,4-dioxane, dimethyl carbonate, tetrahydrofuran, 1,2-dimethoxyethane, diglyme, benzene, cyclohexane, xylene or toluene. More preferably, the solvent is selected from dimethyl formamide, diethyl formamide, dimethylacetamide(DMAc), 1,3-dimethyl-3,4,5,6-tetrahydro-2(1H)-pyrimidinone (DMPU), 1,3-dimethyl-2-imidazolidinone (DMEU or DMI), 3-methyl-2-oxazolidinone, diethylacetamide, 1-methyl-2-pyrrolidinone, hexamethylphosphoric triamide, pyridine, tetramethyl urea, dimethylsulfoxide, acetonitrile, propionitrile, benzonitrile, acetone, 2-butanone, 3-pentanone, acetophenone, nitromethane, nitrobenzene, tetrahydrothiophene 1,1-dioxide (sulfolane), diethyl ether, diisopropyl ether, 1,4-dioxane, tetrahydrofuran, 1,2-dimethoxyethane or diglyme. Most preferably, the solvent is selected from dimethyl formamide, diethyl formamide, dimethylacetamide (DMAc), 1,3-dimethyl-3,4,5,6-tetrahydro-2(1H)-pyrimidinone (DMPU), 1,3-dimethyl-2-imidazolidinone (DMEU or DMI), 3-methyl-2-oxazolidinone, diethylacetamide, 1-methyl-2-pyrrolidinone, hexamethylphosphoric triamide, pyridine, tetramethyl urea, dimethylsulfoxide, acetonitrile, propionitrile, nitromethane or tetrahydrothiophene 1,1-dioxide (sulfolane).

Methanol, when present, may be introduced to the reaction mixture from the source of formaldehyde. However, these alcohols should typically be used in conjunction with the solvents as detailed above and should be present in the liquid phase in amounts less than about 50 wt %, preferably, less than about 45 wt %, more preferably, less than about 20 wt % based on the total weight of the liquid phase.

Advantageously, the use of the solvents as described herein may improve the rate of the reaction.

Reactant

The carboxylic acid ester reactant may be cyclic or non-cyclic. Preferably, the carboxylic acid ester reactant is non-cyclic. Preferably, the carboxylic acid ester reactant is of the following formula:

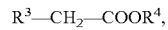

$R^3$—$CH_2$—$COOR^4$, wherein $R^4$ is an alkyl group, preferably a $C_1$ to $C_4$-alkyl group, more preferably, a methyl group, and $R^3$ is hydrogen or a $C_1$ to $C_4$-alkyl group, preferably a methyl group.

Thus, according to a second aspect of the present invention there is provided a process for the production of an ethylenically unsaturated carboxylic acid ester, preferably an α,β ethylenically unsaturated carboxylic acid ester, by the reaction of formaldehyde or a suitable source thereof with a non-cyclic carboxylic acid ester in the presence of a basic metal methyl carbonate co-reactant, wherein the process produces a second basic metal salt and wherein the process includes the step of contacting the second basic metal salt with:

a) carbon dioxide ($CO_2$) and optionally, methanol, and/or
b) dimethyl carbonate, to regenerate the basic metal methyl carbonate co-reactant.

Preferably, the carboxylic acid ester according to any aspect of the present invention is methyl propionate.

Products

Preferably, the ethylenically unsaturated carboxylic acid ester produced by the process of the present invention is selected from methyl methacrylate, ethyl methacrylate, propyl methacrylate or butyl methacrylate or the metal salt of methacrylic acid, most preferably, methyl methacrylate or the metal salt of methacrylic acid.

The process of the invention is particularly suitable for the production of alkyl esters of methacrylic acid. Suitably, esters of methacrylic acid are ($C_1$-$C_4$)alkyl methacrylates, typically produced from the reaction of the corresponding propionic acid ester with formaldehyde or a suitable source thereof in the presence of the basic metal salt, preferably, the production of methyl methacrylate (MMA) from methyl propionate.

Advantageously, the process of the present invention has been found to produce remarkably low levels of unwanted side products in the reaction of formaldehyde or a suitable source thereof with a non-cyclic carboxylic acid ester to produce an ethylenically unsaturated carboxylic acid ester.

Advantageously, it has been shown that the selectivity for ethylenically unsaturated carboxylic acid ester product of the process of the present invention does not substantially decrease with increased rates of conversion as would normally be expected. Typically, in processes of the prior art selectivity decreases as the rate of conversion increases due, without being bound by theory, to the production of more unwanted side products during the reaction at said higher rates of conversion. However, in the process of the present invention remarkably low levels of unwanted side products are produced and, therefore, the process of the present invention has surprisingly been found to produce improved rates of conversion whilst maintaining, or improving, selectivity for the ethylenically unsaturated carboxylic acid ester product.

Furthermore, the major by-product of the present invention is the methanol adduct to the methacrylate ester (methyl 3-methoxyisobutyrate) or the base metal salt of the methanol adduct to methacrylic acid (metal 3-methoxyisobutyrate). These can be converted readily to the corresponding methacrylate by a base catalysed process (either in situ or in a separate process). Therefore, these by-products do not lead to irreversible selectivity loss and can necessarily be discounted when calculating the overall selectivity of the reaction.

Separation and/or purification of the ethylenically unsaturated carboxylic acid ester, preferably α,β ethylenically unsaturated carboxylic acid ester, from unreacted carboxylic acid ester reactant may be performed by any suitable method known in the art.

Preferably, in a batch process the step of removing the ethylenically unsaturated carboxylic acid ester, preferably an α,β ethylenically unsaturated carboxylic acid ester is performed at the end of the reaction.

Preferably, in a continuous reaction the step of removing the ethylenically unsaturated carboxylic acid ester, preferably an α,β ethylenically unsaturated carboxylic acid ester may be performed at any suitable time(s) throughout the process or may be performed in a continuous manner.

Reaction Conditions

The process of the present invention may optionally include an initial step prior to the reaction of formaldehyde or a suitable source thereof with a carboxylic acid ester in the presence of a basic metal methyl carbonate co-reactant. Preferably, the process of the present invention may optionally include an initial step of reacting formaldehyde or a suitable source thereof with a carboxylic acid ester in the presence of a first basic metal salt co-reactant prior to the process according to the first or second aspects of the present invention.

Preferably, the first basic metal salt co-reactant may be a group I or a group II metal salt. Preferably, the first basic metal salt co-reactant may be selected from group I or group II metal oxides, hydroxides, carbonates, hydrogen carbonates, methyl carbonates, alkoxides, such as methoxides and t-butoxides, fluorides and phosphates, more preferably, the first basic metal salt co-reactant is selected from group I or group II metal methoxides, carbonates or methyl carbonates. For the avoidance of doubt, by group I metals as used herein is meant lithium (Li), sodium (Na), potassium (K), rubidium (Rb), and caesium (Cs). For the avoidance of doubt, by group II metals as used herein is meant beryllium (Be), magnesium (Mg), calcium (Ca), strontium (Sr), barium (Ba). Preferably, the group I or group II metal is selected from potassium (K), caesium (Cs), rubidium (Rb) or barium (Ba), more preferably, from caesium (Cs) or rubidium (Rb). Most preferably, the group I or group II metal is selected from caesium (Cs).

Preferably, the first basic metal salt co-reactant may be selected from potassium oxide, caesium oxide, sodium oxide, rubidium oxide, barium oxide, potassium hydroxide, caesium hydroxide, sodium hydroxide, rubidium hydroxide, barium hydroxide, potassium phosphate, caesium phosphate, sodium phosphate, rubidium phosphate, barium phosphate, sodium methoxide, potassium methoxide, rubidium methoxide, sodium t-butoxide, potassium t-butoxide, rubidium t-butoxide, caesium t-butoxide, sodium fluoride, potassium fluoride, rubidium fluoride, caesium fluoride, potassium carbonate, caesium carbonate, sodium carbonate, rubidium carbonate, barium carbonate, potassium hydrogen carbonate, sodium hydrogen carbonate, rubidium hydrogen carbonate, caesium hydrogen carbonate, barium hydrogen carbonate, more preferably, caesium methoxide, rubidium methoxide, caesium carbonate, rubidium carbonate, most preferably, caesium carbonate.

Preferably, the production of the ethylenically unsaturated carboxylic acid ester, preferably α,β ethylenically unsaturated carboxylic acid ester, may be performed at a temperature below about 300° C., more preferably, below about 280° C., most preferably, below about 240° C., especially, below about 190° C., for example, from about 80° C. to 250° C., more preferably from about 100° C. to 200° C., especially from about 120° C. to 190° C. Advantageously, the process of the present invention can be carried out at lower temperatures than would typically be expected from the prior art describing the gas phase reactions. This is particularly surprising given that the deprotonation of methyl propionate (MeP) in its reaction with formaldehyde occurs at high temperatures in industrial processes.

Preferably, the production of the ethylenically unsaturated carboxylic acid ester, preferably α,β ethylenically unsaturated carboxylic acid ester, may be performed at a pressure of between about 5 and 2000 psi, more preferably, between about 10 and 1000 psi, most preferably, between about atmospheric pressure or 14 and 500 psi. Typically, the pressure may be selected such that the reactants are kept dissolved in the liquid phase at a given temperature.

The reagents may be fed to the reactor independently or after prior mixing.

The formaldehyde or suitable source thereof may be added to the reactor containing a liquid phase comprising the carboxylic acid ester together with the dissolved basic metal salt at any suitable rate. Typically, in a batch process the formaldehyde or suitable source thereof is added to the reactor containing a liquid phase comprising the carboxylic acid ester together with the dissolved basic metal salt at a rate which is suitable to maintain the carboxylic acid ester in a molar excess compared to the said formaldehyde or suitable source thereof.

By "molar excess" as used herein is meant, unless otherwise specified, that the formaldehyde or suitable source thereof is present in amounts at least 1 mol % lower, preferably, at least 5 mol % lower, more preferably, at least 10 mol % lower than the amount of carboxylic acid ester based on the total amount of formaldehyde or suitable source thereof and carboxylic acid ester present in the liquid phase.

For example, in a batch process the formaldehyde or suitable source thereof may be added to the reactor at a rate from about 1 to 10 mol %/minute relative to the carboxylic acid ester.

Preferably, the molar ratio of formaldehyde or suitable source thereof to the carboxylic acid ester is maintained at about 1:100 to 1:2, more preferably, about 1:50 to 1:5 throughout the duration of the process.

Preferably, in a batch reaction the molar ratio of basic metal salt to the carboxylic acid ester added to the liquid phase is about 5:1 to 0.2:1, more preferably, the molar ratio is about 2:1 to 0.4:1, most preferably, the molar ratio is about 2:1 to 0.5:1.

Preferably, the liquid phase composed of the carboxylic acid ester, basic metal salt and optional solvent is heated to around the temperature at which the reaction will be performed prior to addition of the formaldehyde or suitable source thereof. Preferably, the formaldehyde or suitable source thereof is heated to around the temperature at which the reaction will be performed prior to mixing with the liquid phase. It will be appreciated by a person skilled in the art that the liquid phase composed of the carboxylic acid ester, basic metal salt and optional solvent may be heated to a temperature 30° C. above or below the temperature at which the reaction will be performed.

Typically, during a continuous process the formaldehyde or suitable source thereof is added to the reactor, containing a liquid phase comprising the carboxylic acid ester together with the dissolved basic metal salt, at a rate which maintains the carboxylic acid ester in a molar excess compared to the said formaldehyde or suitable source thereof in the liquid phase. In a continuous reaction the formaldehyde or suitable source thereof may be fed to the liquid phase comprising the carboxylic acid ester and the dissolved basic metal salt together with further carboxylic acid ester reactant and/or the basic metal salt.

For the avoidance of doubt, the term "molar excess" as used in reference to a continuous reaction has the same meaning as described above for a batch reaction.

Preferably, in a continuous reaction the formaldehyde or suitable source thereof may be fed to the reactor in a molar ratio of 1.1:1 to 1:1 with the carboxylic acid ester.

Preferably, in a continuous reaction the molar ratio of basic metal salt to the carboxylic acid ester may be maintained at 5:1 to 0.2:1, more preferably, about 2:1 to 0.4:1, most preferably, about 2:1 to 0.5:1 in the liquid phase.

Advantageously, in either a batch or a continuous reaction, adding the formaldehyde or suitable source thereof to the reactor in the manner as defined above, surprisingly, results in an improved rate of conversion. Advantageously, adding the formaldehyde or suitable source thereof to the reactor in the manner as defined above, surprisingly, limits the build up of formaldehyde thus reducing unwanted side reactions producing unwanted side products.

Advantageously, without being bound by theory, the addition of formaldehyde or suitable source thereof to the liquid phase containing the carboxylic acid ester together with the dissolved basic metal methyl carbonate co-reactant and optional solvent enables the formaldehyde to be heated to reaction temperature without any risk of decomposition catalysed by the basic metal methyl carbonate co-reactant.

In a batch reaction, contact times for the reactants in the presence of the basic metal methyl carbonate co-reactant are dependent on temperature, pressure and the concentration of the basic metal salt but are typically between 2 minutes and 12 hours, more preferably, 5 minutes and 8 hours, most preferably, 10 minutes and 4 hours.

In a continuous reaction average residence times in the reactor may correspond to the contact times in a batch reaction as set out above.

The amount of basic metal methyl carbonate co-reactant used in the process of the present invention is not necessarily critical and will be determined by the practicalities of the process in which it is employed. However, the amount of base will generally be chosen to effect the optimum selectivity and yield. Nevertheless, the skilled person will appreciate that the minimum amount of base should be sufficient to bring about sufficient deprotonation of the carboxylic acid ester to permit an acceptable rate of the reaction.

The relative amount of reagents used in or fed to the process of the invention can vary within wide limits but generally the mole ratio of formaldehyde or suitable source thereof to the carboxylic acid ester is within the range of 1:20 to 2:1, more preferably, 1:10 to 1.5:1, most preferably, 1:5 to 1.2:1. The most preferred ratio will depend on the form of the formaldehyde and the ability of the base to liberate formaldehyde from the formaldehydic species. Thus highly reactive formaldehydic substances where one or both of $R^{31}$ and $R^{32}$ in $R^{31}O-(CH_2-O-)_tR^{32}$ is H require relatively low ratios, typically, in this case, the mole ratio of formaldehyde or suitable source thereof to the carboxylic acid ester is within the range of 1:9 to 1:1. Where the formaldehydic substances are of low reactivity, for instance where neither of $R^{31}$ and $R^{32}$ is H, as for instance in $CH_3O-CH_2-O-CH_3$, or in trioxane higher ratios are most preferred, typically, 1:9 to 20:1.

The process according to any aspect of the present invention may optionally further comprise one or more alcohol(s). Preferably, an optional alcohol(s) for use in the basic reaction of the present invention is methanol. The amount of methanol is not critical. Generally, the amount used is as low as practicable allowing for its presence in some sources of formaldehyde, unless methanol is chosen as a reaction solvent as well, although, if desired, separate or further solvents may also be used.

The molar ratio of alcohol, when present in the reaction, to the carboxylic acid ester is typically within the range 20:1 to 1:20, preferably 3:1 to 1:10, most preferably 2:1 to 1:5.

The molar ratio of methanol, when present in the reaction, to the carboxylic acid ester is typically within the range 20:1 to 1:20, preferably 3:1 to 1:10, most preferably 2:1 to 1:5.

Drying Agents

As mentioned above, due to the source of formaldehyde, water may also be present in the reaction mixture. Depending on the source of formaldehyde, it may be necessary to remove some or all of the water therefrom prior to reaction. As mentioned above, maintaining lower levels of water than that in the source of formaldehyde may be advantageous to the reaction efficiency and/or subsequent purification of the products.

Therefore, the process of the present invention may optionally further comprise one or more drying agents. Suitable drying agents include anhydrous sodium sulphate, anhydrous magnesium sulphate, molecular sieves (various pore sizes), calcium oxide, calcium chloride, potassium carbonate, oxazolidines, orthoesters of the general formula $RC(OR)_3$, aluminum oxide, silica gel, activated carbon, montmorillonite and mixtures thereof.

Alternatively, or additionally, the process of the present invention may optionally comprise a dehydration step. Preferably, the optional dehydration step may be performed before the step of contacting the second basic metal salt with carbon dioxide ($CO_2$) and optionally, methanol, and/or dimethyl carbonate or after the step of contacting the second basic metal salt with carbon dioxide ($CO_2$) and optionally, methanol, and/or dimethyl carbonate, more preferably, before the step of contacting the second basic metal salt with carbon dioxide ($CO_2$) and optionally, methanol, and/or dimethyl carbonate.

The dehydration step, when used, may be performed by any suitable method. In one embodiment, the dehydration step, when used, may be performed by dissolving the liquid phase in methanol followed by passing the resultant solution through a molecular sieve. In an alternative embodiment, the dehydration step, when used, may be performed by flash distillation.

In a continuous process, the dehydration step, when used, may optionally include the step of carbon dioxide ($CO_2$) capture. Advantageously, the use of a carbon dioxide ($CO_2$) capture step means that captured carbon dioxide ($CO_2$) may be recycled into the process of the present invention. For example, when flash distillation is used, a step of carbon dioxide ($CO_2$) capture may be included after the flash distillation has been performed.

Definitions

The term "alkyl" when used herein, means, unless otherwise specified, $C_1$ to $C_{12}$ alkyl and includes methyl, ethyl, ethenyl, propyl, propenyl butyl, butenyl, pentyl, pentenyl, hexyl, hexenyl and heptyl groups, preferably, methyl, ethyl, propyl, butyl, pentyl and hexyl. Unless otherwise specified, alkyl groups may, when there is a sufficient number of carbon atoms, be linear or branched, be cyclic, acyclic or part cyclic/acyclic, be unsubstituted, substituted or terminated by one or more substituents selected from halo, cyano, nitro, —$OR^{19}$, —$OC(O) R^{20}$, —$C(O)R^{21}$, —$C(O) OR^{22}$, —$NR^{23}R^{24}$, —$C(O) NR^{25}R^{26}$, —$SR^{29}$, —$C(O)SR^{30}$, —$C(S)NR^{27}R^{28}$, unsubstituted or substituted aryl, or unsubstituted or substituted Het, wherein $R^{19}$ to $R^{30}$ here and generally herein each independently represent hydrogen, halo, unsubstituted or substituted aryl or unsubstituted or substituted alkyl, or, in the case of $R^{21}$, halo, nitro, cyano and amino and/or be interrupted by one or more (preferably less than 4) oxygen, sulphur, silicon atoms, or by silano or dialkylsilcon groups, or mixtures thereof. Preferably, the alkyl groups are unsubstituted, preferably, linear and preferably, saturated.

The term "alkenyl" should be understood as "alkyl" above except at least one carbon carbon bond therein is unsaturated and accordingly the term relates to $C_2$ to $C_{12}$ alkenyl groups.

The term "alk" or the like should, in the absence of information to the contrary, be taken to be in accordance with the above definition of "alkyl".

The term "aryl" when used herein includes five-to-ten-membered, preferably five to eight membered, carbocyclic aromatic or pseudo aromatic groups, such as phenyl, cyclopentadienyl and indenyl anions and naphthyl, which groups may be unsubstituted or substituted with one or more substituents selected from unsubstituted or substituted aryl, alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O) SR^{30}$ or $C(S) NR^{27}R^{28}$ wherein $R^{19}$ to $R^{30}$ each independently represent hydrogen, unsubstituted or substituted aryl or alkyl (which alkyl group may itself be unsubstituted or substituted or terminated as defined herein), or, in the case of $R^{21}$, halo, nitro, cyano or amino.

The term "halo" when used herein means a chloro, bromo, iodo or fluoro group, preferably, chloro or fluoro.

The term "Het", when used herein, includes four- to twelve-membered, preferably four- to ten-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, alkyl (which alkyl group may itself be unsubstituted or substituted or terminated as defined herein) —$OR^{19}$, —$OC(O) R^{20}$, —$C(O) R^{21}$, —$C(O)OR^{22}$, —$N(R^{23})R^{24}$, —$C(O)N(R^{25})R^{26}$, —$SR^{29}$, —$C(O)SR^{30}$ or —$C(S)N(R^{27})R^{28}$ wherein $R^{19}$ to $R^{30}$ each independently represent hydrogen, unsubstituted or substituted aryl or alkyl (which alkyl group itself may be unsubstituted or substituted or terminated as defined herein) or, in the case of $R^{21}$, halo, nitro, amino or cyano. The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

The terms "base" or "basic" when used herein, means, unless otherwise specified, a chemical species or molecular entity having at least one available pair of electrons capable of forming a covalent bond with hydrogen (proton) or with the vacant orbital of another species. The base may be a Brønsted base or a Lewis base. For the avoidance of doubt, a Brønsted base is a chemical species or molecular entity capable of accepting a hydrogen (proton) from an acid (i.e. a hydrogen acceptor) or the corresponding molecular entity or chemical species. For the avoidance of doubt, a Lewis base is a chemical species or molecular entity able to provide a pair of electrons and thus capable of coordination to a Lewis acid, thereby producing a Lewis adduct.

The term "homogenous" as used herein means, unless otherwise specified, a process in which all the components, such as the reactants, the basic metal salt and, when present, the solvent are in the same phase.

The term "heterogenous" as used herein means, unless otherwise specified, a process in which one or more of the components, such as the reactants, the basic metal salt and, when present, the solvent are in a different phase from the remaining components.

The term "batch process" as used herein means, unless otherwise specified, a process in which a specified amount of reactants are reacted to obtain product under reaction conditions. The reaction generally continues until the reactants are used up.

The term "continuous process" as used herein means, unless otherwise specified, a process in which the reactants are fed into the reactor and products are taken out of the reactor after commencement of reaction and during the process. The reaction generally continues until the reactor is shut down.

The term "co-reactant" as used herein means, unless otherwise specified, a component which is consumed along with other reactants during the reaction.

According to a further aspect of the present invention there is provide the use of a) carbon dioxide ($CO_2$) and optionally, methanol, and/or b) dimethyl carbonate, to regenerate a basic metal methyl carbonate co-reactant from a second basic metal salt which has been produced during the production of an ethylenically unsaturated carboxylic acid ester, preferably an α,β ethylenically unsaturated carboxylic acid ester, by the reaction of formaldehyde or a suitable source thereof with a carboxylic acid ester in the presence of a basic metal methyl carbonate co-reactant.

BRIEF DESCRIPTION OF DRAWINGS

Embodiments of the invention will now be described with reference to the following non-limiting examples and figures and by way of illustration only in which:—

WORKING EXAMPLES

Example 1

Figure 1:
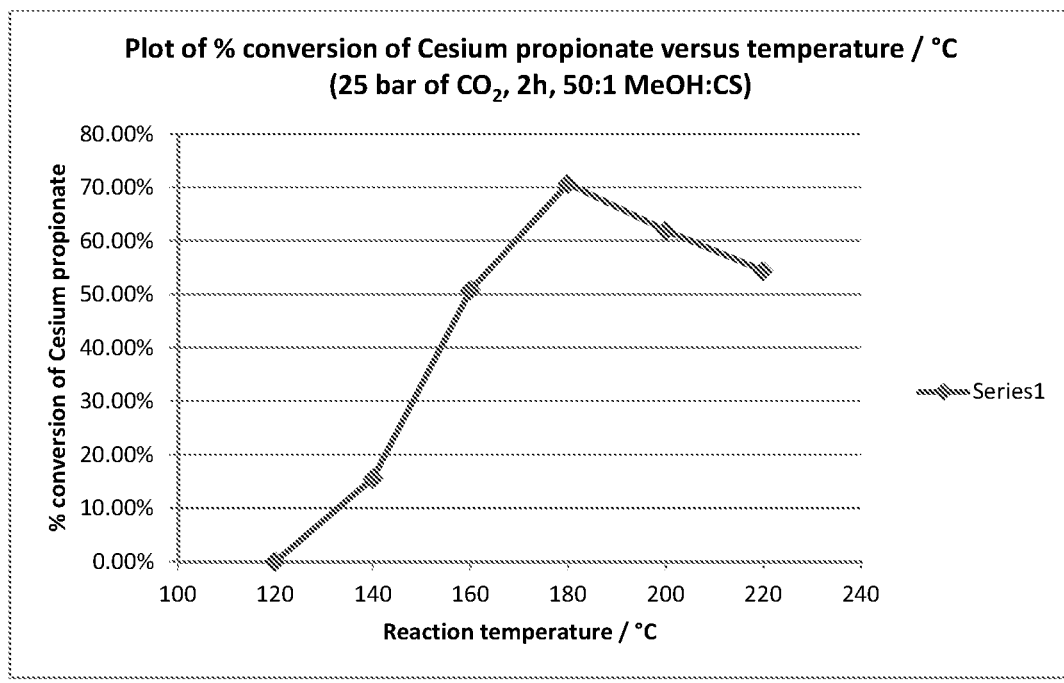
FIG. 1 shows a plot of conversion of caesium propionate versus temperature

The exit mixture of non-volatile salts from the reaction of formaldehyde and methyl propionate in the presence of caesium methyl carbonate (containing approximately 57% caesium propionate, 22% caesium methacrylate and 21% caesium methyl carbonate) was charged to an autoclave. The autoclave was pressurized slowly with carbon dioxide to a pressure of 40 bar and then sealed. The mixture was heated to a reaction temperature of 180° C. for 2 hours and was then cooled to room temperature. The residual pressure was released slowly. The exit mixture was analysed using $^1H$ and $^{13}C\{^1H\}$ NMR spectroscopy in $d_4$-methanol. Results are shown in Table 1.

TABLE 1

| Run number | Entry | Caesium methyl carbonate/% | Caesium propionate/% | Caesium methacrylate/% |
| --- | --- | --- | --- | --- |
| 1 | non-volatile salts | 21 | 57 | 22 |
| 2 | End of run 1 | 64 | 17 | 20 |
| 3 | End of run 2 | 81 | 5 | 14 |
| 4 | End of run 3 | 87 | 1 | 12 |
| 5 | End of run 4 | 93 | trace | 7 |

The results show that substantially all of the caesium propionate is converted to caesium methyl carbonate after five (5) regeneration runs.

Example 2

Caesium propionate was dissolved in 9 ml methanol to form a 5 mmol solution and added to a reactor. The reactor was then charged with $CO_2$ to a pressure of 15 bar and sealed. The reaction mixture was heated to a temperature of 160° C. over a time period of 1 hour (temperature ramping at 2° C./min). Once the reaction mixture had reached this temperature, the reaction was allowed to proceed for 2 hours. The conversion to Caesium methyl carbonate was measured.

Examples 3-9

Example 2 was repeated with the exception that variable basic metal salts, $CO_2$ pressures and temperatures were used according to Table 2.

TABLE 2

| Example no. | Basic metal salt at start of reaction | $CO_2$ Pressure/Bar | Temperature/° C. | Reaction time/hours | Conversion to metal methyl carbonate/% |
| --- | --- | --- | --- | --- | --- |
| 2 | CsP | 15 | 160 | 2 | 36 |
| 3 | CsP | 40 | 160 | 2 | 43 |
| 4 | CsP | 40 | 180 | 2 | 71 |
| 5 | CsP‡ | 40 | 200 | 2 | 88 |
| 6 | RbP | 40 | 200 | 2 | 81 |
| 7 | KP | 40 | 200 | 2 | 88 |
| 8 | CsMA | 40 | 200 | 2 | 63 |
| 9 | CsP* | 40 | 160 | 2 | 29 |

*reaction run with 2 mL of DMAc

All examples show that the reactivation of a basic metal salt, i.e. the formation of a metal methyl carbonate from a metal propionate or methacrylate salt, is possible.

Regeneration Experiments with Caesium Propionate

Further regeneration reactions were performed on samples of Caesium propionate in methanol The reaction variables that were examined for their effect on reaction conversion were:
1. Reaction temperature and
2. $CO_2$ pressure.

For each set of data the conversions reported are based upon the NMR analysis of the reaction exit solutions.

Example 10

Examination of the Effect of Reaction Temperature on the Conversion of CsP to CsMC (Runs 1-6)

The dependence of the conversion of CsP to CsMC on reaction temperature was examined. All reactions were performed at 25 bar $CO_2$ pressure, with a molar ratio of 1:50 CsP:MeOH and a reaction time of two hours. The temperature was varied for each run with reactions performed at each of 120° C., 140° C., 160° C., 180° C., 200° C. and 220° C. (runs 1-6, respectively). The results are shown in FIG. 1.

As shown in FIG. 1, no conversion occurs at 120° C. but as the reaction temperature is increased there is a steady increase in conversion, peaking at 72% conversion at 180° C. There is a decrease in conversion when the temperature is raised above 180° C.

Example 11

Examination of the Effect of $CO_2$ Pressure on the Conversion of CsP to CsMC (Runs 7-13)

The next variable considered was the $CO_2$ pressure charged into the autoclave at the start of the reaction. All reactions were performed with a molar ratio of 1:50 CsP:MeOH, a reaction temperature of 160° C. and a reaction time of two hours. The pressure was varied for each run with reactions performed at each of 10, 15, 20, 25, 30, 35 and 39 bar (runs 7-13, respectively). After the $CO_2$ was added the pressure always fell due to the gas dissolving into the methanol solvent. As the temperature of the reaction mixture was increased, the reactor pressure increased as expected. All reported values for the pressures of carbon dioxide are for the pressures charged into the autoclave at the start of the experiment when the contents are at room temperature. The results are shown in FIG. 2.

Figure 2:
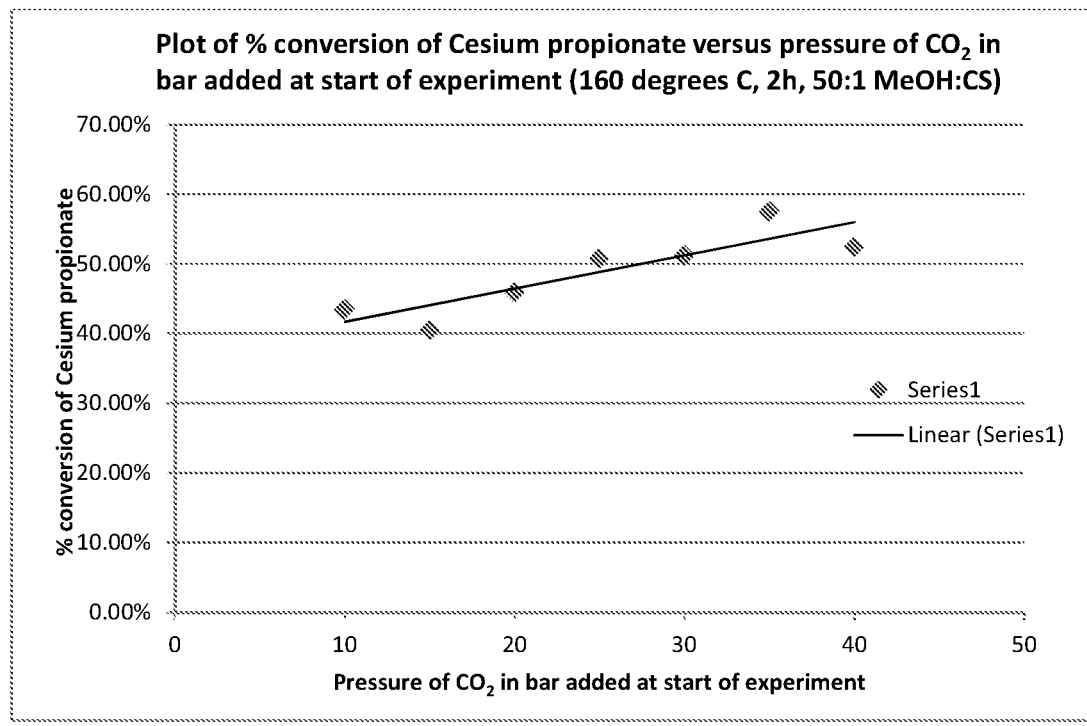
FIG. 2 shows a plot of conversion of caesium propionate versus pressure of carbon dioxide

As shown in FIG. 2, greater conversions of Caesium propionate to Caesium methyl carbonate were achieved when the $CO_2$ charging pressure was increased.

There is a general upward trend in conversion. Raising the pressure from 10 to 40 bar in the CsP experiments yielded a 10% increase in conversion.

Regeneration Experiments with Caesium Methacrylate

The reaction variables that were examined for their effect on reaction conversion of caesium propionate were also tested for the conversion of caesium methacrylate.

For each set of data the conversions reported are based upon the NMR analysis of the reaction exit solutions.

Example 12

Examination of the Effect of Temperature Upon the Reaction of Solutions of Caesium Methacrylate in Methanol (Runs 14-19)

The dependence of the conversion of CsMA to CsMC on reaction temperature was the first variable to be examined. All reactions were performed at 25 bar $CO_2$ pressure, with a molar ratio of 1:50 CsMA:MeOH and a reaction time of two hours. The temperature was varied for each run with reactions performed at each of 120° C., 140° C., 160° C., 180° C., 200° C. and 220° C. (runs 14-19, respectively). The results are shown in FIG. 3.

Figure 3:
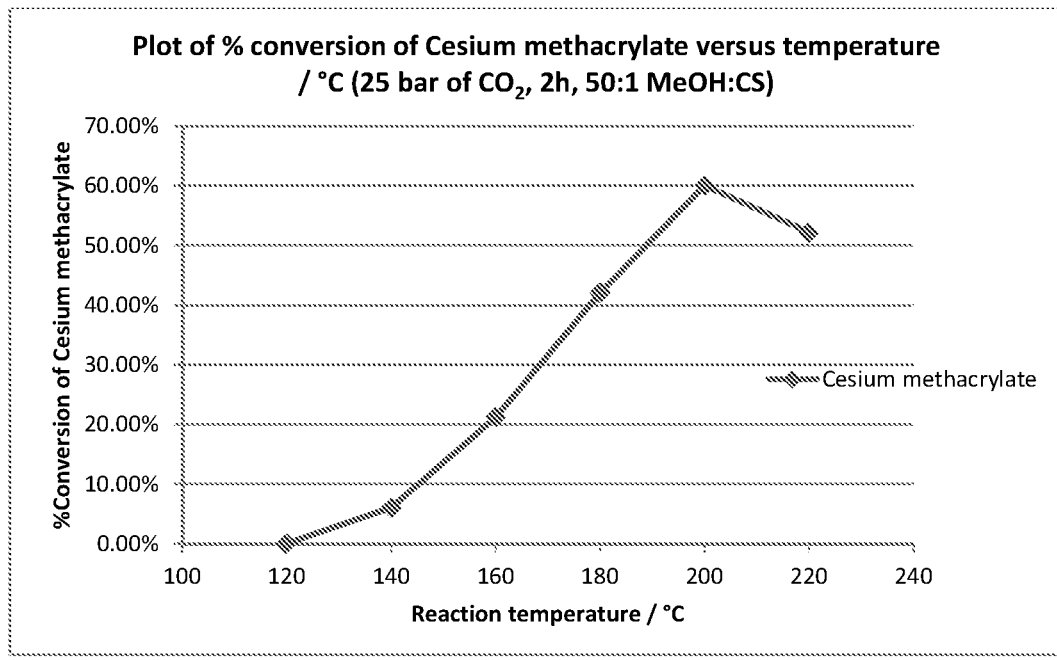
FIG. 3 shows a plot of conversion of caesium methacrylate versus temperature

As shown in FIG. 3, no conversion occurs at 120° C. but as the reaction temperature is increased there is a steady increase in conversion, peaking at 60% conversion at 200° C. There is a decrease in conversion when the temperature is raised above 200° C.

Figure 4:
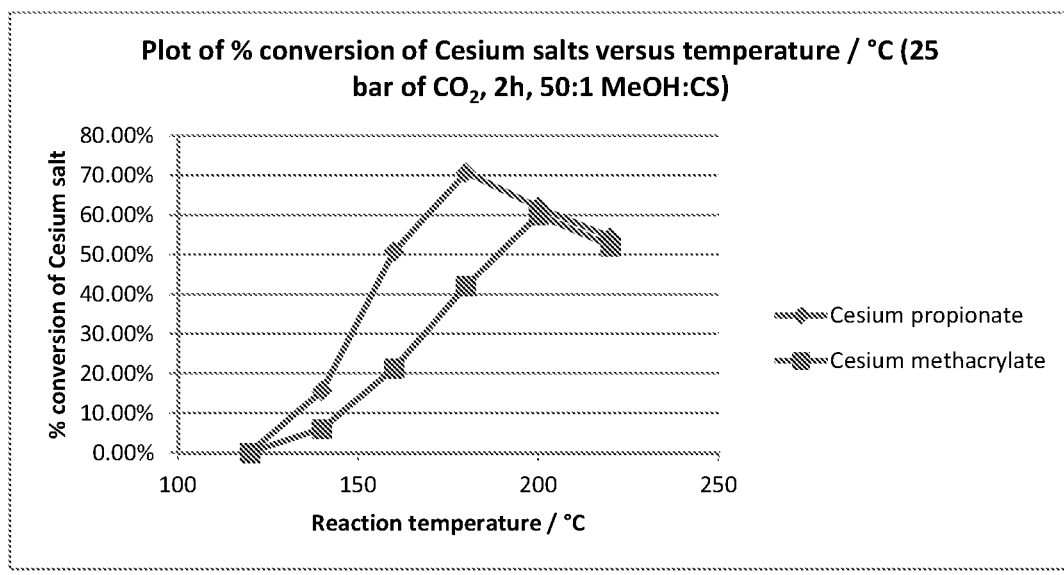
FIG. 4 shows a plot of conversion of caesium salt versus temperature

The temperature effect on the degree of conversion of the two Caesium salts (methacrylate and propionate) is compared in FIG. 4.

Example 13

Examination of the Effect of $CO_2$ Pressure Upon the Reaction of Solutions of Caesium Methacrylate in Methanol (Runs 20-22)

The next variable considered was the $CO_2$ pressure charged into the autoclave at the start of the reaction. All reactions were performed with a molar ratio of 1:50 CsMA: MeOH, a reaction temperature of 160° C. and a reaction time of two hours. The pressure was varied for each run with reactions performed at each of 10, 15, 20, 25, 30, 35 and 39 bar (runs 20-22, respectively). All reported values for the pressures of carbon dioxide are for the pressures charged into the autoclave at the start of the experiment when the contents are at room temperature. The results are shown in FIG. 5.

Figure 5:
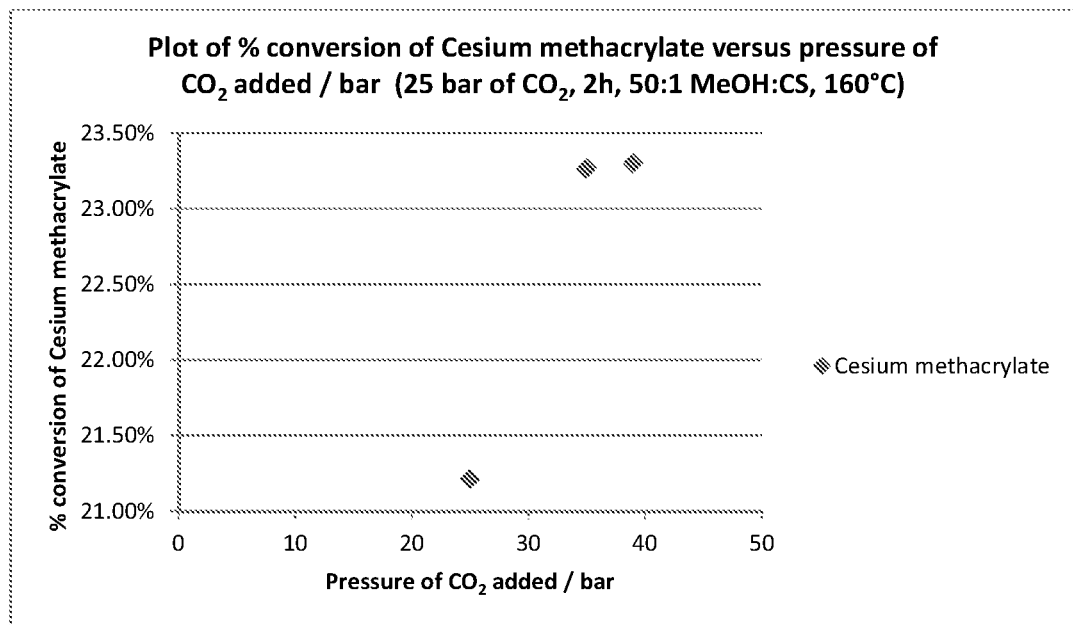
FIG. 5 shows a plot of conversion of caesium methacrylate versus pressure of carbon dioxide

As shown in FIG. 5, for the three pressures of $CO_2$ added at the start of the experiment (25 bar, 35 bar and 39 bar) very little change in the degree of conversion of Caesium methacrylate was observed.

Figure 6:
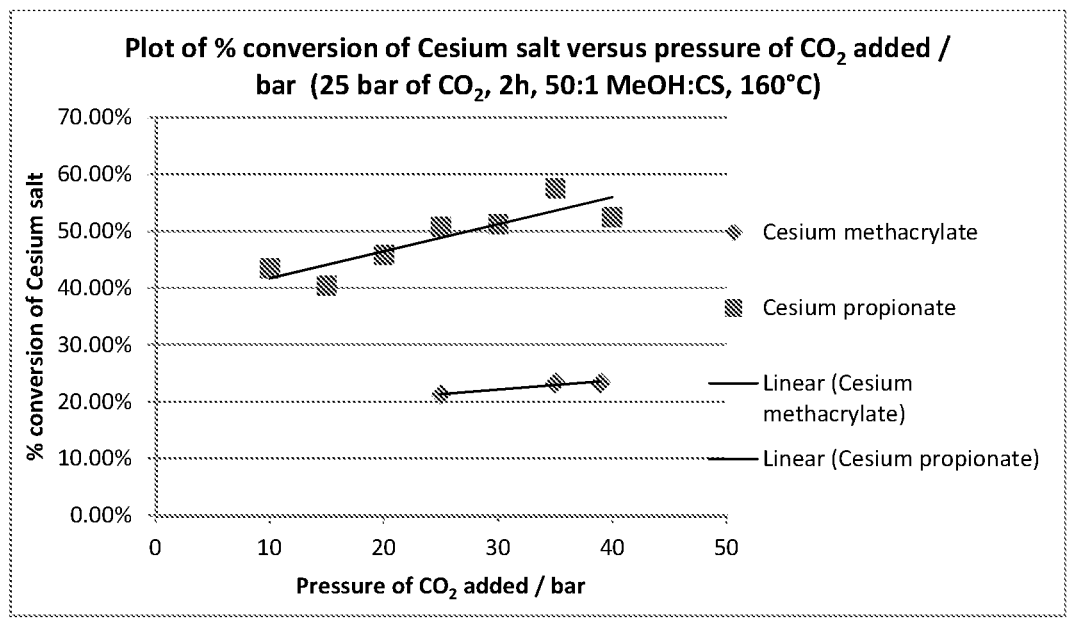
FIG. 6 shows a plot of conversion of caesium salt versus pressure of carbon dioxide.

Comparison of the effect of carbon dioxide pressure on the conversion of the Caesium salts, Caesium propionate and Caesium methacrylate is shown in FIG. 6.

Example 14

Regeneration Experiments Carried Out with Multiple Caesium Salts (Runs 23-24)

An actual exit mixture from the condensation reaction of MeP and formaldehyde employing CsMC as the reaction catalyst will contain mixtures of Cs salts that will need to be converted back to CsMC.

Experiments were carried out using mixtures of Caesium propionate and Caesium methacrylate to determine whether or not they compete in the regeneration reaction for the available methanol and carbon dioxide. The % conversion of CsP and CsMA to CsMC was carried out with methanol solutions containing 1:1 molar mixtures of CsP and CsMA. The experiments were carried out with 25 bar of $CO_2$ and for a reaction time of two hours. The experiments were carried out at 160° C. and 180° C. The results from these experiments are shown in Table 3.

TABLE 3

| Run number | Temperature/ ° C. | Mixtures from runs 23 and 24 | | Single Component experiments | |
| --- | --- | --- | --- | --- | --- |
| | | % Conversion of CsMA | % Conversion of CsP | % Conversion of CsMA | % Conversion of CsP |
| 23 | 160 | 20% | 48% | 17% | 51% |
| 24 | 180 | 37% | 75% | 42% | 71% |

The results in Table 3 show, within experimental error, that the level of conversion of the Caesium propionate and Caesium methacrylate salts is the mixed salt experiments is similar to that observed in the single salt experiments.

Example 15

Regeneration Experiments Using Dimethyl Carbonate

Into a 1 L Hastelloy autoclave was added methyl propionate (62.04 g, 0.70 moles), Cesium methoxycarbonate (56.57 g, 0.27 moles), N,N-Dimethylacetamide (127.10 g, 1.46 moles) and dimethyl carbonate (68.47 g, 0.76 moles). The autoclave was then sealed, pressure tested and then heated to 160° C. At this temperature methyl alcoform (55 weight % formaldehyde, 36.90 ml, 0.68 moles) was added at a rate of 1.23 ml/min for a period of thirty minutes. The autoclave was then heated for a further ninety minutes before being cooled to room temperature.

The contents of the autoclave were then vacuum distilled to remove all of the volatile compounds with a boiling point lower than the dimethyl acetamide. This leaves as a reaction residue the dimethyl acetamide and the Caesium salts. The volatile compounds were weighed and analysed using an Agilent GC. This allowed the determination of the number of moles of methyl methyacrylate in the volatile compounds.

The residue from the vacuum distillation was suspended in a mixture of methyl propionate (62.04 g, 0.70 moles) and dimethyl carbonate (68.47 g, 0.76 moles) and this mixture was the feed for the autoclave.

An autoclave experiment was then carried out with this mixture in the same manner as the initial experiment.

Overall seven experiments were carried out in this way (runs 1-7) and the number of moles of MMA produced in each cycle and the cumulative number of moles is shown in Table 4.

TABLE 4

| Cycle number | Moles of MMA produced |
| --- | --- |
| 1 | 0.08 |
| 2 | 0.12 |
| 3 | 0.06 |
| 4 | 0.13 |
| 5 | 0.13 |

TABLE 4-continued

| Cycle number | Moles of MMA produced |
|---|---|
| 6 | 0.14 |
| 7 | 0.13 |
| Cumulative moles of MMA produced | 0.79 |

What can be observed from Table 4 is that starting with 0.27 moles of the Caesium catalyst, Caesium methoxy carbonate, 0.79 moles of MMA has been produced in these recycling experiments. This shows that the catalyst has been fully recycled three times over the seven recycling experiments and that there is no apparent decline in the amount of MMA produced in each cycle as the number of cycles increases.

CONCLUSIONS

A number of Caesium methyl carbonate regeneration experiments have been carried out using both single and multi-component systems containing Caesium propionate and Caesium methacrylate. A number of conclusions can be drawn from the experimental results.

In both the experiments with Caesium propionate and Caesium methacrylate, increasing the reaction temperature increases the level of conversion until a plateau temperature at which the level of conversion decreases.

In both the experiments with Caesium propionate and Caesium methacrylate, increasing the pressure of carbon dioxide added at the start of the experiments results in an increase in the conversion.

When they were regenerated as part of a mixed system, Caesium propionate and Caesium methacrylate show no signs of being competitive for carbon dioxide and methanol present in the reaction solution.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A process for the production of an ethylenically unsaturated carboxylic acid ester by the reaction of formaldehyde or a suitable source thereof with a carboxylic acid ester in the presence of a basic metal methyl carbonate co-reactant, wherein the process produces a second basic metal salt and wherein the process includes the step of contacting the second basic metal salt with:
   a) carbon dioxide ($CO_2$) and optionally, methanol, and/or
   b) dimethyl carbonate,
to regenerate the basic metal methyl carbonate co-reactant.

2. The process according to claim 1, wherein at least some of the carbon dioxide ($CO_2$) is by-product carbon dioxide ($CO_2$).

3. The process according to claim 1, wherein, when carbon dioxide ($CO_2$) is used, the step of contacting the second basic metal salt with carbon dioxide ($CO_2$) is carried out in the presence of methanol.

4. The process according to claim 3, wherein at least some of the methanol is by-product methanol.

5. The process according to claim 1, wherein the process is a continuous process.

6. The process according to claim 1, wherein the reaction takes place with the reactants and co-reactant dissolved in the liquid phase.

7. The process according to claim 1, wherein the basic metal methyl carbonate co-reactant is a group I or a group II metal methyl carbonate.

8. The process according to claim 7, wherein the basic metal methyl carbonate co-reactant is caesium methyl carbonate.

9. The process according to claim 1, wherein the second basic metal salt is a metal carboxylate of the following formula:

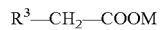

$R^3$—$CH_2$—COOM wherein M is a metal of the basic metal methyl carbonate co-reactant and $R^3$ is hydrogen or a $C_1$ to $C_4$-alkyl group or is a metal carboxylate of the following formula:

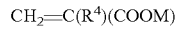

$CH_2$=$C(R^4)(COOM)$ wherein M is a metal of the basic metal methyl carbonate co-reactant and $R^4$ is hydrogen or a $C_1$ to $C_4$-alkyl group.

10. The process according to claim 9, wherein the second basic metal salt is a group I or group II metal salt.

11. The process according to claim 10, wherein the second basic metal salt is a group I or group II metal propionate and/or methacrylate.

12. The process according to claim 10, wherein the second basic metal salt is caesium propionate and/or caesium methacrylate.

13. The process according to claim 1, wherein the step of contacting the second basic metal salt with a) carbon dioxide ($CO_2$) and optionally, methanol, and/or b) dimethyl carbonate is carried out at a temperature below about 250° C.

14. The process according to claim 1, wherein the step of contacting the second basic metal salt with a) carbon dioxide ($CO_2$) and optionally, methanol, and/or b) dimethyl carbonate is carried out at a pressure of between about atmospheric pressure and 2000 psi.

15. The process according to claim 1, wherein the suitable source of formaldehyde is selected from formalin (formaldehyde, methanol, water), low molecular weight polyformaldehyde (paraformaldehyde), gaseous formaldehyde, formaldehyde hemiacetal (alcoform), trioxane or anhydrous formaldehyde, or formaldehyde from a distillative drying process, or other sources of formaldehyde where the level of water is <30% by weight of the level of formaldehyde.

16. The process according to claim 15, wherein the formaldehyde from the distillative drying process is a formaldehyde-containing product obtained by a process comprising distilling a formaldehyde solution in the presence of a water entraining compound, such as methyl propionate, such that the formaldehyde containing product is recovered as a complex with methanol and also typically includes the water entraining compound, most suitably methyl propionate.

17. The process according to claim 1, wherein the process further comprises one or more solvents.

18. The process according to claim 17, wherein the solvent is wholly or substantially aprotic.

19. The process according to claim 18, wherein the solvent is an aprotic protophilic solvent or an aprotic photophobic solvent.

20. The processes according to claim 19, wherein the solvent is selected from dimethyl formamide, diethyl formamide, dimethylacetamide(DMAc), diethylacetamide, 1-methyl-2-pyrrolidinone, hexamethylphosphoric triamide, pyridine, tetramethyl urea, dimethylsulfoxide, acetonitrile, propionitrile, benzonitrile, acetone, 2-butanone, 3-pentanone, acetophenone, nitromethane, nitrobenzene, tetrahydrothiophene 1,1-dioxide (sulfolane), diethyl ether, diisopropyl ether, 1,4-dioxane, tetrahydrofuran, 1,2-dimethoxyethane, diglyme, benzene, cyclohexane, xylene or toluene.

21. The process according to claim 1, wherein the carboxylic acid ester reactant is of the following formula:

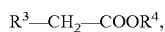

$R^3$—$CH_2$—$COOR^4$, wherein $R^4$ is an alkyl group and $R^3$ is hydrogen or a $C_1$ to $C_4$-alkyl group.

22. The process according to claim 1, further comprising an initial step of reacting formaldehyde or a suitable source thereof with a carboxylic acid ester in the presence of a first basic metal salt co-reactant.

23. The process according to claim 22, wherein the first basic metal salt co-reactant is a group I or a group II metal salt.

24. The processes according to claim 23, wherein the first basic metal salt co-reactant is selected from group I or group II metal oxides, hydroxides, carbonates, hydrogen carbonates, methyl carbonates, alkoxides, such as methoxides and t-butoxides, fluorides and phosphates.

25. The process according to claim 24, wherein the first basic metal salt co-reactant is selected from potassium oxide, caesium oxide, sodium oxide, rubidium oxide, barium oxide, potassium hydroxide, caesium hydroxide, sodium hydroxide, rubidium hydroxide, barium hydroxide, potassium phosphate, caesium phosphate, sodium phosphate, rubidium phosphate, barium phosphate, sodium methoxide, potassium methoxide, rubidium methoxide, sodium t-butoxide, potassium t-butoxide, rubidium t-butoxide, caesium t-butoxide, sodium fluoride, potassium fluoride, rubidium fluoride, caesium fluoride, potassium carbonate, caesium carbonate, sodium carbonate, rubidium carbonate, barium carbonate, potassium hydrogen carbonate, sodium hydrogen carbonate, rubidium hydrogen carbonate, caesium hydrogen carbonate, and barium hydrogen carbonate.

26. The process according to claim 1, wherein the process further comprises a dehydration step.

27. The process according to claim 26, wherein the dehydration step may is performed before the step of contacting the second basic metal salt with a) carbon dioxide ($CO_2$) and optionally, methanol, and/or b) dimethyl carbonate.

28. The process according to claim 26, wherein the dehydration step is performed by dissolving the liquid phase in methanol followed by passing the resultant solution through a molecular sieve or by flash distillation of the liquid phase.

29. The process according to claim 1, wherein the carboxylic acid ester is non-cyclic.

* * * * *